(12) United States Patent
Yoshida

(10) Patent No.: US 11,096,646 B2
(45) Date of Patent: Aug. 24, 2021

(54) X-RAY IMAGING APPARATUS

(71) Applicant: Shimadzu Corporation, Kyoto (JP)

(72) Inventor: Takanori Yoshida, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 57 days.

(21) Appl. No.: 16/810,312

(22) Filed: Mar. 5, 2020

(65) Prior Publication Data

US 2020/0323507 A1    Oct. 15, 2020

(30) Foreign Application Priority Data

Apr. 10, 2019   (JP) .............................. JP2019-075078

(51) Int. Cl.
*A61B 6/00* (2006.01)
*A61B 6/04* (2006.01)

(52) U.S. Cl.
CPC .................. *A61B 6/52* (2013.01); *A61B 6/04* (2013.01); *A61B 6/4452* (2013.01)

(58) Field of Classification Search
None
See application file for complete search history.

(56) References Cited

U.S. PATENT DOCUMENTS

| | | | | | |
|---|---|---|---|---|---|
| 7,715,528 | B2* | 5/2010 | Miura | ..................... | A61B 6/504 378/98.12 |
| 2013/0294674 | A1* | 11/2013 | Miyamoto | ............ | G06T 7/0014 382/132 |
| 2015/0289831 | A1* | 10/2015 | Sakaguchi | ........... | A61B 6/5205 600/431 |
| 2018/0368793 | A1* | 12/2018 | Goto | ....................... | A61B 6/484 |
| 2019/0274651 | A1* | 9/2019 | Ohashi | ....................... | G06T 5/50 |

FOREIGN PATENT DOCUMENTS

| | | |
|---|---|---|
| JP | 5029607 B2 | 9/2012 |
| WO | 2017/104067 A1 | 6/2017 |

* cited by examiner

*Primary Examiner* — Hoon K Song
(74) *Attorney, Agent, or Firm* — Muir Patent Law, PLLC

(57) ABSTRACT

This X-ray imaging apparatus includes a control unit for performing control to select one blood vessel image in which a blood vessel is clearly reflected from a plurality of blood vessel images stored in the storage unit when capturing a fluoroscopic image and performing control to display a superimposed image in which the selected blood vessel image and the fluoroscopic image are superimposed on the display unit.

9 Claims, 12 Drawing Sheets

X-RAY IMAGING APPARATUS

CROSS-REFERENCE TO RELATED APPLICATIONS

The related application number JP2019-075078, entitled "X-ray imaging apparatus", filed on Apr. 10, 2019, and invented by Takanori Yoshida upon which this patent application is based is hereby incorporated by reference.

BACKGROUND OF THE INVENTION

Field of the Invention

The present invention relates to an X-ray imaging apparatus, and more particularly to an X-ray imaging apparatus for displaying a superimposed image in which a blood vessel image and a fluoroscopic image are superimposed on a display unit.

Description of the Background Art

Conventionally, there has been known an X-ray imaging apparatus for displaying a blood vessel image and a fluoroscopic image on a display unit in a superimposed manner with respect to an X-ray imaging apparatus. Such an X-ray fluoroscopic apparatus is disclosed, for example, in WO 2017/104067.

The X-ray imaging apparatus disclosed in WO 2017/104067 is provided with an X-ray irradiation detection unit, a top board for placing a subject thereon, and an image synthesis unit. The image synthesis unit generates a first X-ray image as a long image in which images captured by sequentially performing X-ray imaging using a contrast agent while relatively moving a top board with respect to the X-ray irradiation detection unit are connected and a second X-ray image obtained by performing X-ray imaging of a subject at a position corresponding to a position of a part of a long image selected based on the first X-ray image without using a contrast agent. Then, a synthetic image is generated by subtracting the created second image from the created first image. Furthermore, the X-ray imaging apparatus disclosed in WO 2017/104067 synthesizes by superimposing the synthetic image in which the first X-ray image and the second X-ray image are synthesized on a fluoroscopic image for treatment.

SUMMARY OF THE INVENTION

In the case of generating a long image as described in WO 2017/104067, a plurality of images (blood vessel images) including a relative position coordinate of the same X-ray irradiation detection unit and top board is captured and connected. Although not described in the above-described WO 2017/104067, in cases where there is a plurality of blood vessel images including the same relative position coordinate, it is considered that one blood vessel image selected from the plurality of blood vessel images including the same relative position coordinate is used for generating a long image. However, there is a possibility that the selected blood vessel image is not an image in which a blood vessel is not clearly reflected compared with unselected blood vessel images. For this reason, even if the fluoroscopic image and the blood vessel image include the same relative position coordinate, there is a possibility that the blood vessel is not clearly reflected in the selected blood vessel image. Also, unlike WO 2017/104067, although a long image is not generated, also in cases where there is a plurality of blood vessel images, there is a possibility that an image selected as an image including the same relative position coordinate as a fluoroscopic image does not clearly reflect a blood vessel.

The present invention has been made to solve the above-mentioned problems, and aims to provide an X-ray imaging apparatus capable of easily selecting a blood vessel image including the same relative position coordinate as a fluoroscopic image and clearly reflecting a blood vessel image from a plurality of blood vessel images.

In order to achieve the above object, an X-ray imaging apparatus according to one aspect of the present invention includes:

a top board configured to place a subject thereon;

an imaging unit including an X-ray source configured to irradiate the subject placed on the top board with X-rays and a detection unit configured to detect X-rays transmitted through the subject and output a detection signal;

an image processing unit configured to generate a plurality of blood vessel images sequentially captured by administering a contrast agent to a blood vessel so that a plurality of images includes the same relative position coordinate while changing a relative position between the imaging unit and the top board and generate a fluoroscopic image captured at a timing different from timings of the plurality of blood vessel image images;

a storage unit configured to store the plurality of blood vessel images;

a display unit configured to display an image generated by the image processing unit; and a control unit configured to perform at least one of control to select one blood vessel images in which the blood vessel is most clearly reflected from the plurality of blood vessel images including the same relative position coordinate as an imaging position of the fluoroscopic image stored in the storage unit when the fluoroscopic image is captured and control to generate one blood vessel image in which the blood vessel is clearly reflected compared with each of the plurality of blood vessel images including the same relative position coordinate as the imaging position of the fluoroscopic image stored in the storage unit, and to perform control to display a superimposed image in which a selected or generated vessel image and the fluoroscopic image are superimposed on the display unit.

According to the present invention, the X-ray imaging apparatus is provided with a control unit configured to perform at least one of control to select one blood vessel image in which the blood vessel is most clearly reflected from the plurality of blood vessel images including the same relative position coordinate as an imaging position of the fluoroscopic image stored in the storage unit when the fluoroscopic image is captured and control to generate one blood vessel image in which the blood vessel is clearly reflected compared with each of the plurality of blood vessel images including the same relative position coordinate as the imaging position of the fluoroscopic image stored in the storage unit, and to perform control to display a superimposed image in which a selected or generated vessel image and the fluoroscopic image are superimposed on the display unit. With this, it is possible to select a blood vessel image in which the same relative positional coordinate as the relative positional coordinate of the fluoroscopic image is included and the blood vessel is clearly reflected. As a result, this makes it possible to easily select a blood vessel image in which the same relative position coordinate as a fluoroscopic image is included and a blood vessel is clearly reflected from a plurality of blood vessel images. In addition, by generating one blood vessel image in which a blood vessel is clearly reflected compared with each of the plurality of blood vessel images including the relative position coordinate, it is possible to assuredly obtain an image in which a blood vessel is clearly reflected.

DESCRIPTION OF THE PREFERRED EMBODIMENT (Configuration of X-Ray Imaging Apparatus)

Figure 1:
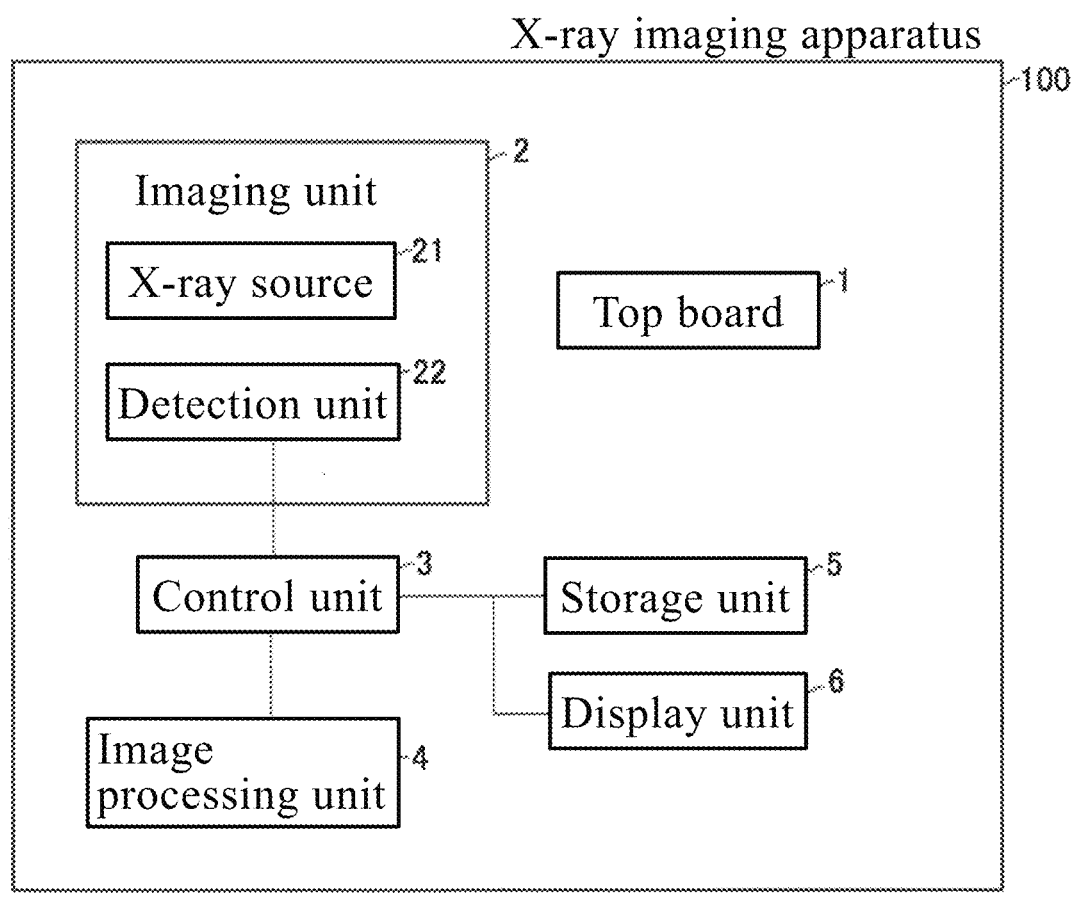
FIG. 1 is a diagram showing an entire configuration of an X-ray imaging apparatus.
Figure 2:
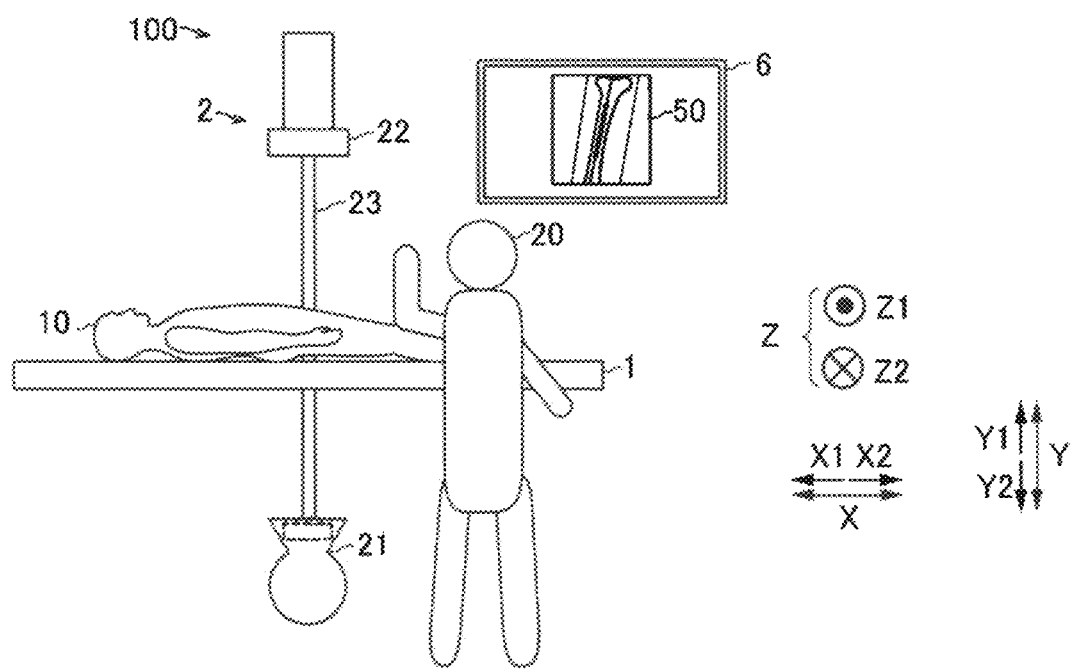
FIG. 2 is a diagram showing the X-ray imaging apparatus.

Referring to FIG. 1 and FIG. 2, the entire configuration of an X-ray imaging apparatus 100 according to an embodiment of the present invention will be described.

As shown in FIG. 1, the X-ray imaging apparatus 100 according to this embodiment is provided with a top board 1, an imaging unit 2 including an X-ray source 21 and a detection unit 22, a control unit 3, an image processing unit 4, a storage unit 5, and a display unit 6.

As shown in FIG. 2, the top board 1 is formed in a rectangular flat plate shape in a plan view. A subject 10 is placed on the top board 1 such that the head-foot direction of the subject 10 is along the long side of the rectangle and the left-right direction of the subject 10 is along the short side of the rectangle. In this specification, the head-foot direction of the subject 10 is defined as an X-direction, the left-right direction of the subject 10 is defined as a Z-direction, and the direction perpendicular to the X-direction and the Z-direction is defined as a Y-direction.

The top board 1 is provided with a moving mechanism (not shown). The X-ray imaging apparatus 100 can capture an image of the subject 10 while changing the relative position between the top board 1 and the imaging unit 2 by moving the top board 1 in the longitudinal direction (X-direction) by a moving mechanism. A plurality of position coordinates indicating the top board position is set on the top board 1.

The imaging unit 2 is provided with an X-ray source 21, a detection unit 22, and an arm 23 in which the X-ray source 21 and the detection unit 22 are arranged so as to face each other. A plurality of position coordinates indicating the position of the imaging unit 2 is set on the arm 23. It is configured such that the blood vessel image 40 captured while changing the relative position between the top board 1 and the imaging unit 2 (see FIG. 3) is stored in the storage unit 5 in a state in which the relative position coordinate Xn acquired from the position coordinate of the top board 1 and the position coordinate of the arm 23 are in association with each other. It is also configured such that the blood vessel image 40 is stored in the storage unit 5 in association with a plurality of relative position coordinates corresponding to the position coordinate of the top board 1 in addition to the relative position coordinate Xn which is the coordinate indicating the imaging position. The relative position coordinate Xn of the imaging position can be, for example, a relative position coordinate that can be obtained from the position coordinate of the top board 1 at the position in which the optical axis of the X-rays emitted from the X-ray source 21 and the top board 1 intersect and the position coordinate of the arm 23.

The X-ray source 21 emits X-rays when voltage is applied by a drive unit (not shown). The X-ray source 21 has a collimator capable of adjusting the irradiation field, which is an irradiation range of X-rays. In this embodiment, the X-ray source 21 is attached to one side tip end of the arm 23.

The detection unit 22 is attached to the other side tip end of the arm 23. That is, the detection unit 22 is disposed on the other side of the X-ray source 21 with the top board 1 interposed therebetween. The detection unit 22 is configured to detect X-rays. The detection unit 22 is composed of, for example, an FPD (flat panel detector). The detection unit 22 is configured to detect X-rays that have passed through the subject 10 and output a detection signal based on the detected X-rays.

The control unit 3 is composed of a computer including a CPU (Central Processing Unit), a ROM (Read Only Memory), and a RAM (Random Access Memory).

The image processing unit 4 is composed of a computer including a processor, such as, e.g., a GPU (Graphics Processing Unit) or an FPGA (Field-Programmable Gate Array) configured to process images. The image processing unit 4 functions as an image processing apparatus by executing an image processing program.

The storage unit 5 is a ROM provided in the control unit 3. The storage unit 5 is configured to store a blood vessel image 40 generated by the image processing unit 4.

The display unit 6 is a monitor included in the X-ray imaging apparatus 100. The display unit 6 is configured to display an image generated by the image processing unit 4.

(Usage of X-Ray Imaging Apparatus)

As shown in FIG. 2, the X-ray imaging apparatus 100 of this embodiment is used when a user 20 performs diagnosis and/or treatment of a subject 10. In this embodiment, a case is described in which a user 20 performs diagnosis and treatment of a blood vessel 11 of a lower limb of a subject 10.

Figure 5:
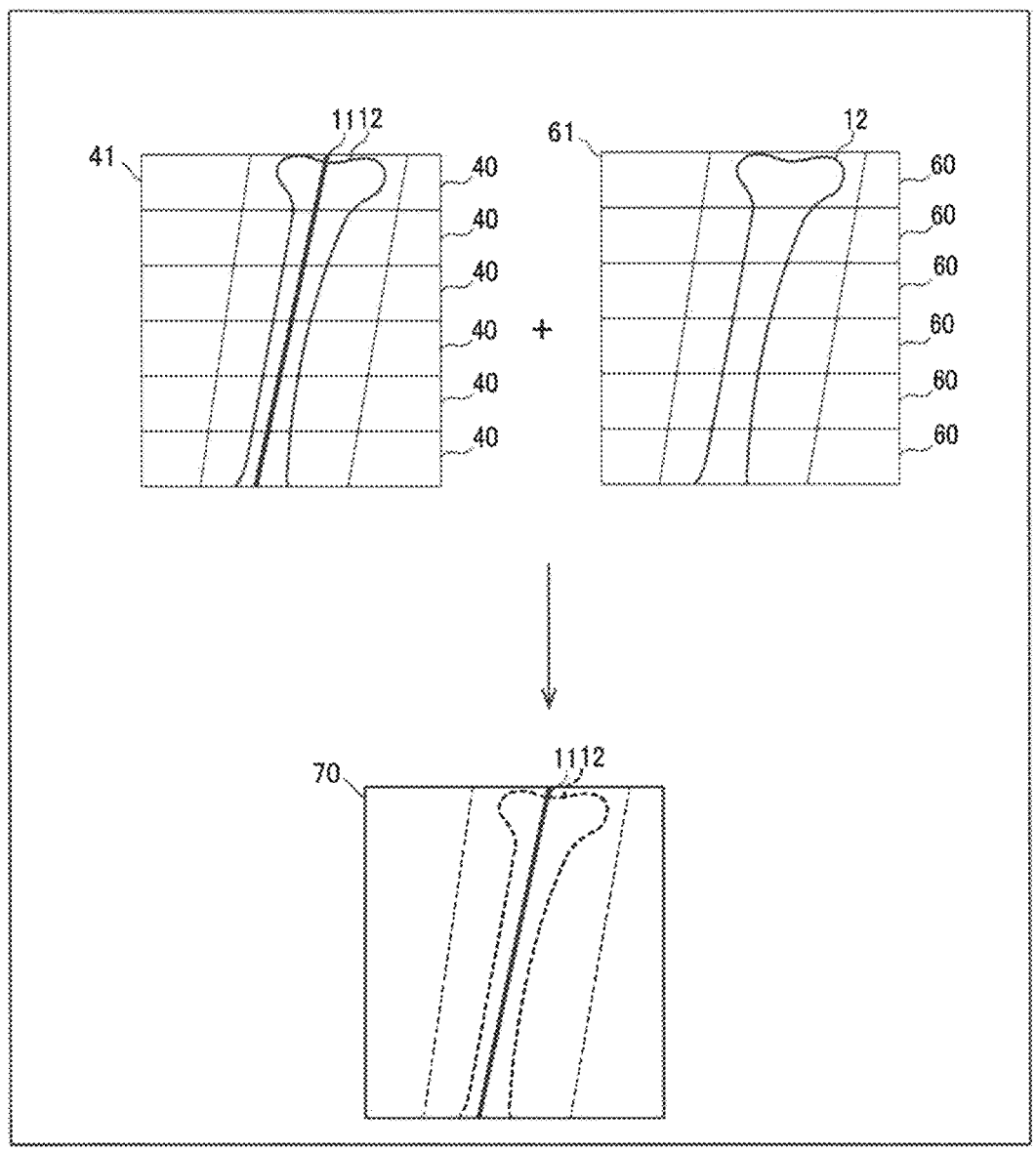
FIG. 5 is a diagram showing an example of a differential long image.

As shown in FIG. 5, when diagnosing, a user 20 captures a differential long image 70 for specifying a treatment position of a blood vessel 11 of a lower limb of the subject 10.

Figure 3:
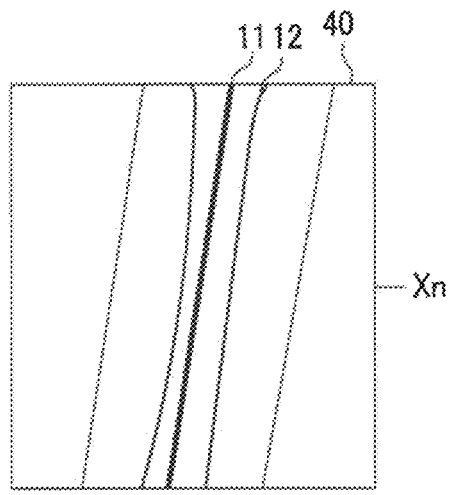
FIG. 3 is a diagram showing an example of a blood vessel image.

As shown in FIG. 1 to FIG. 3, a user 20 captures a plurality of blood vessel images 40 while administering a contrast agent to a subject 10 placed on the top board 1 and changing the relative position between the imaging unit 2 and the top board 1. Before administering a contrast agent, there is no difference between the attenuation of the X-rays transmitted through the blood vessel 11 and the attenuation of the X-rays transmitted through the surrounding tissue, so that a blood vessel image 40 clearly reflecting a blood vessel 11 is not generated. Therefore, by administering a contrast agent for shielding X-rays to the subject 10, the attenuation of the X-rays transmitted through the blood vessel 11 and the attenuation of the X-rays transmitted through the surrounding tissue become different from each other, which enables to generate a blood vessel image 40 which clearly reflects the blood vessel 11. Note that in FIG. 3, it is assumed that the blood vessel 11 is simplified and illustrated by a straight line and the blood vessel 11 is positioned above a bone 12. At this time, the capturing of the blood vessel image 40 is performed in accordance with the flow of the contrast agent. It is configured such that the plurality of captured blood vessel images 40 is stored in the storage unit 5.

Figure 4:
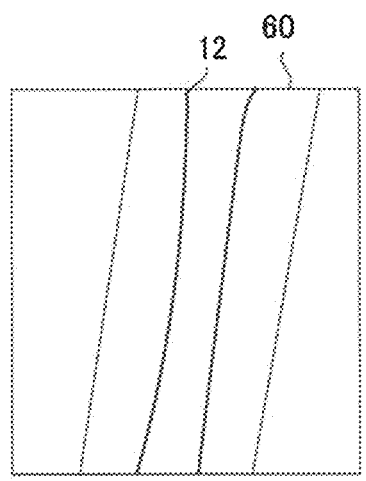
FIG. 4 is a diagram showing an example of a non-contrast agent image.

As shown in FIG. 1, FIG. 2, and FIG. 4, after capturing the blood vessel images 40, the user 20 captures a plurality of non-contrast agent images 60 without administering a contrast agent to the subject 10. The storage unit 5 is storing imaging conditions, such as, e.g., the moving rate of the top board 1 at the time of capturing the blood vessel images 40, the frame rate of the imaging, and the radiation dose to be irradiated, and the control unit 3 is configured to perform control to capture non-contrast agent images 60 under the same imaging condition as the imaging condition of the blood vessel image 40 stored in the storage unit 5.

As shown in the upper left diagram of FIG. 5, the image processing unit 4 is configured to extract parts of a plurality of captured blood vessel images 40 and generate a first long image 41 obtained by connecting them.

As shown in the upper right diagram of FIG. 5, the image processing unit 4 is configured to extract parts of a plurality of captured non-contrast agent images 60 and generate a second long image 61 obtained by connecting them. In the upper right diagram of FIG. 5, no blood vessel 11 is illustrated to indicate that the blood vessel 11 is unclear.

As shown in the lower center diagram of FIG. 5, the image processing unit 4 is configured to generate a differential long image 70 by taking the difference between the first long image 41 and the second long image 61. The differential long image 70 is an image in which common portions other than the blood vessel 11 are made obscure by subtracting the non-contrast agent image 60 captured at the same imaging position with the blood vessel 11 obscurely reflected from the blood vessel image 40 reflecting the blood vessel 11 and portions other than the blood vessel 11 (e.g., bone 12). In the lower center view of FIG. 5, the obscurely reflected portions (e.g., bone 12) are illustrated by dashed lines to indicate that portions other than the blood vessel 11 have become obscured. Note that the first long image 41 is an example of the "long image" recited in claims.

As shown in FIG. 1 and FIG. 5, the control unit 3 is configured to perform control to display the generated differential long image 70 on the display unit 6. Then, the user 20 determines the treatment position based on the displayed differential long image 70, and starts fluoroscopic imaging for treatment.

In this embodiment, the X-ray imaging apparatus 100 is configured to perform two fluoroscopic imaging operations, i.e., fluoroscopic imaging for generating a superimposed image 50 and a fluoroscopic imaging for performing treatment.

Figure 10:
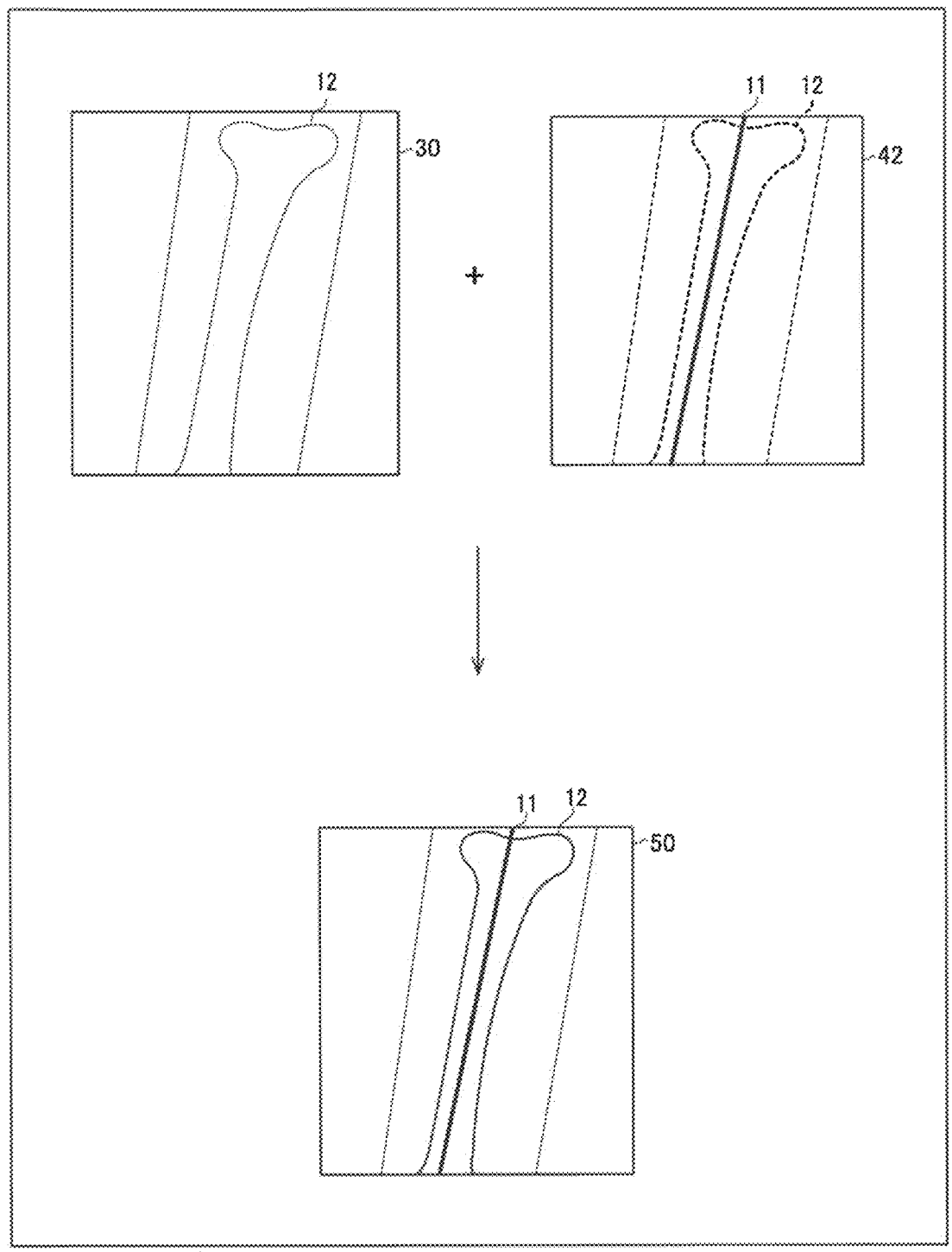
FIG. 10 is a diagram showing another example of a superimposed image.

The X-ray imaging apparatus 100 of this embodiment can switch between the setting for superimposing a fluoroscopic image 30 and a blood vessel image 40 (see FIG. 8) and the setting for superimposing a fluoroscopic image 30 and a peak hold image 42 configured by extracting the minimum pixel value from a plurality of blood vessel images 40 for each relative position coordinate Xn (see FIG. 10). By switching the settings, the image processing unit 4 is configured to switch the image to be superimposed on the fluoroscopic image 30 between the blood vessel image 40 and the peak hold image 42.

Referring to FIG. 1, FIG. 2, FIG. 6, FIG. 7, FIG. 8, and FIG. 9, the case in which the X-ray imaging apparatus 100 is set to superimpose the fluoroscopic image 30 and the blood vessel image 40 will be explained.

Figure 7:
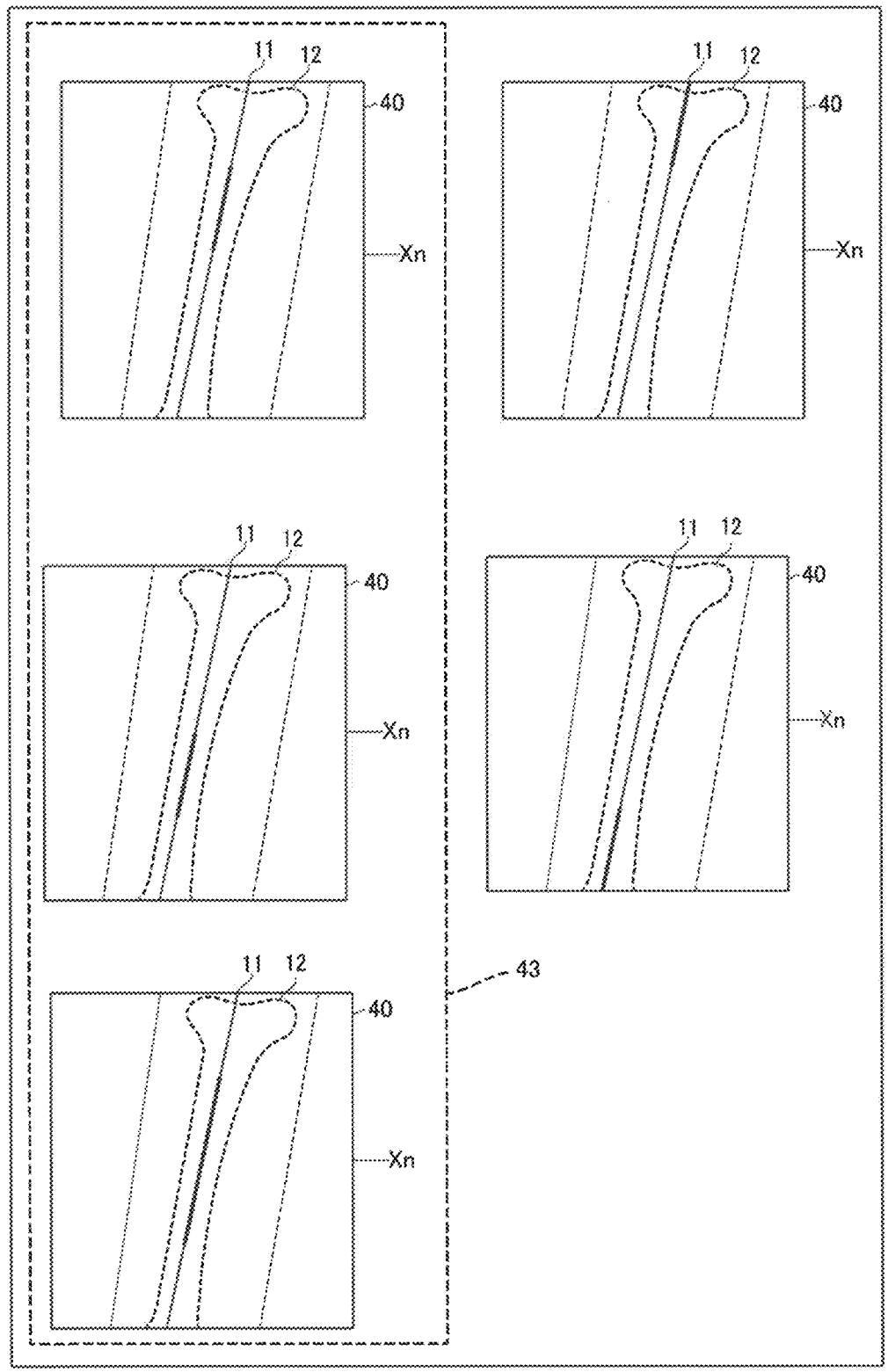
FIG. 7 is a diagram showing an example of a blood vessel image group.

As shown in FIG. 1 and FIG. 7, a user 20 selects a blood vessel image 40 at the treatment location from a plurality of blood vessel images 40. Upon receipt of an input from the user 20, the control unit 3 performs control to move the imaging position of fluoroscopic imaging to the imaging position of the selected blood vessel image 40 by moving the top board 1.

After moving the top board 1, the control unit 3 is configured to perform control to emit X-rays from the X-ray source 21 to the subject 10. The X-rays transmitted through the subject 10 are detected by the detection unit 22, and a detection signal is output.

As shown in FIG. 2, the control unit 3 is configured to perform control the image processing unit 4 to generate a fluoroscopic image 30 based on the detection signal. The fluoroscopic image 30 generated by the image processing unit 4 is associated with a relative position coordinate Xn based on the position coordinate of the top board 1 and the position coordinate of the arm 23.

Figure 6:
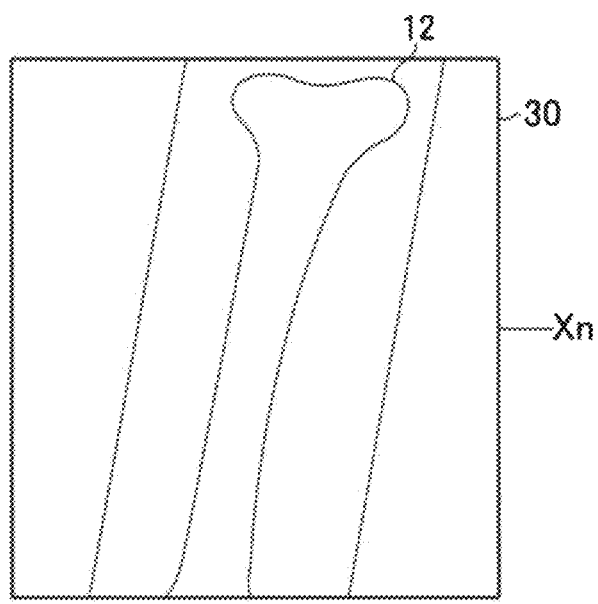
FIG. 6 is a diagram showing an example of a fluoroscopic image.

As shown in FIG. 1, FIG. 6, and FIG. 7, the control unit 3 is configured to perform control of a first selection to select a blood vessel image group 43 composed of a plurality of blood vessel images 40 having the same relative position coordinate Xn as the relative position coordinate Xn of the imaging position of the fluoroscopic image 30 from the storage unit 5. In FIG. 7, the portion where the pixel value of the blood vessel 11 is relatively low is illustrated by a thick line. Further, in FIG. 7, the portion having a lower pixel value of the blood vessel 11 is different for each blood vessel image 40. As shown in FIG. 6, the relative position coordinate Xn of the imaging position is a relative position coordinate Xn of the center of the fluoroscopic image 30.

Figure 8:
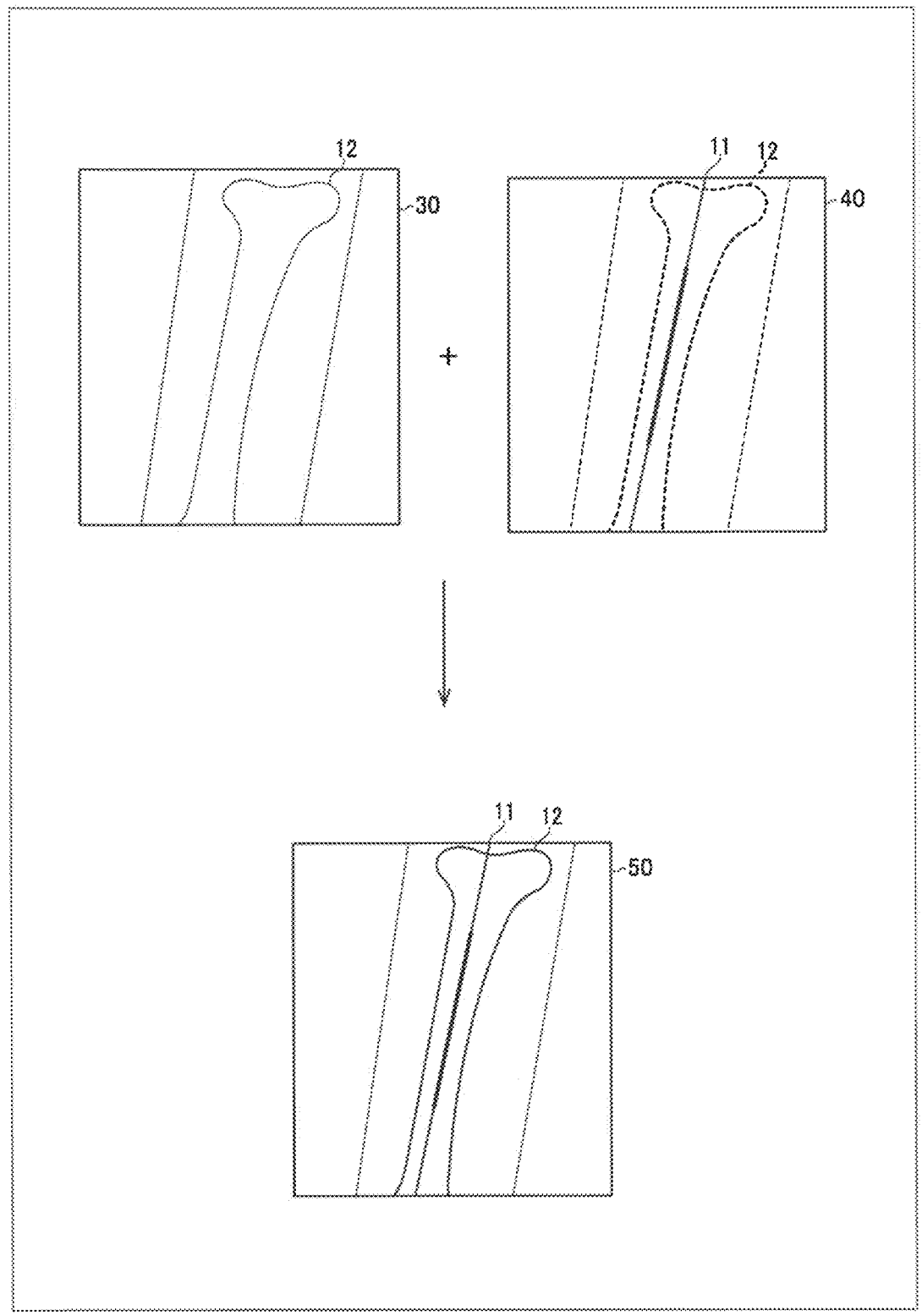
FIG. 8 is a diagram showing an example of a superimposed image.

As shown in FIG. 8, the control unit 3 is configured to perform control of a second selection to select a blood vessel image 40 in which the sum of pixel values at the relative position coordinate Xn and therearound is the lowest from the blood vessel image group 43 selected from the storage unit 5. Before performing the control of the second selection, the image processing unit 4 is configured to perform a process of unifying pixel values of the background of the blood vessel image 40. In the blood vessel image 40 where a large amount of a contrast agent is contained, since the pixel value is lowered by the contrast agent, if the background pixel value is the same, the sum of pixel values is lowered in proportion to the amount of the contrast agent. Thus, the control unit 3 is configured to obtain the sum of pixel values of the relative position coordinate Xn and therearound for each blood vessel image 40 and select a blood vessel image 40 in which the sum of pixel values is the lowest. The range surrounding the relative position coordinate Xn may be set to the entirety of the blood vessel image 40, and may be set to a certain range from the center of the blood vessel image 40 assuming that the relative position coordinate Xn is positioned at or near the center of the blood vessel image 40.

Figure 9:
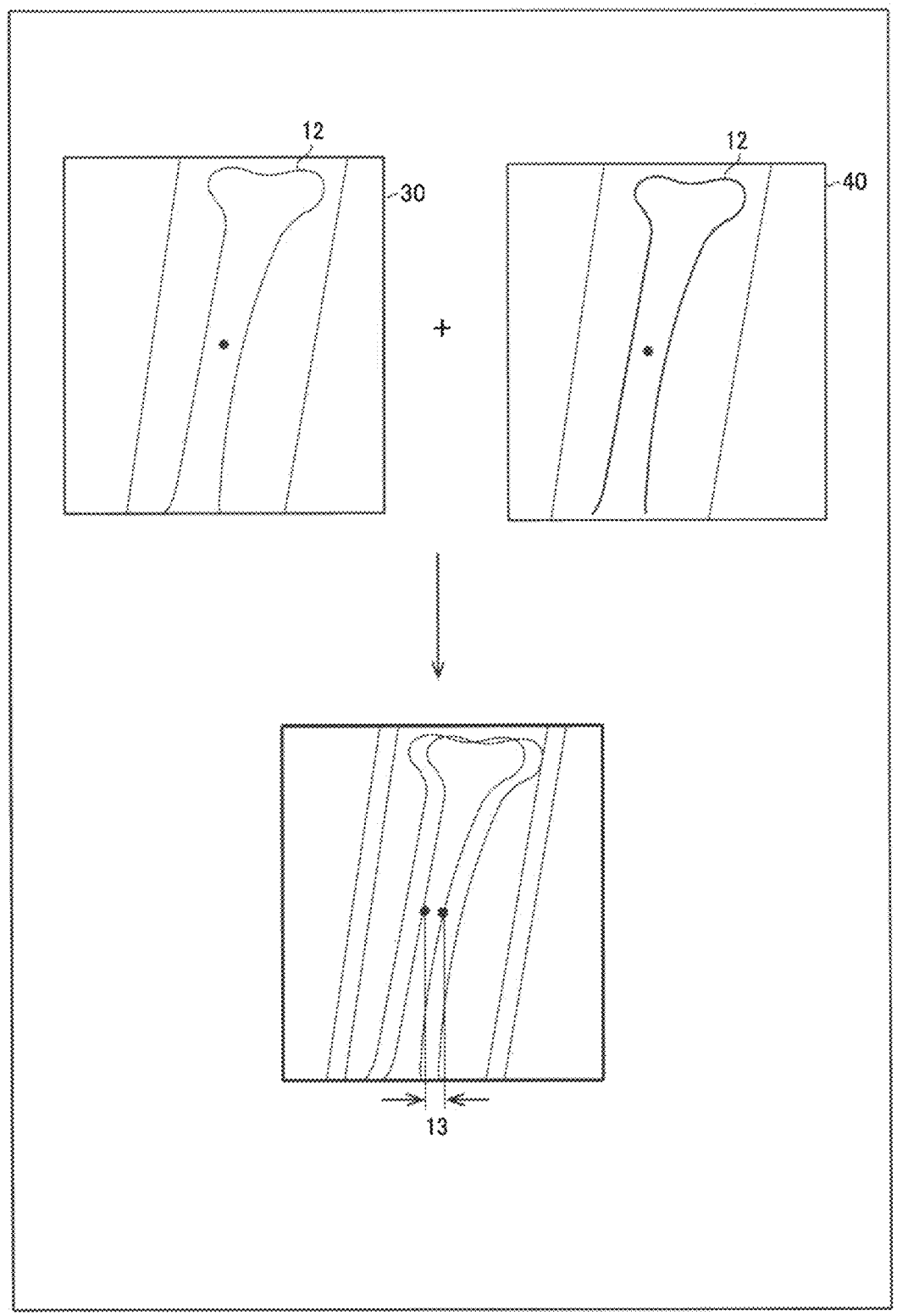
FIG. 9 is a diagram for explaining a moving amount.

As shown in FIG. 9, the control unit 3 is configured to acquire a moving amount 13 (shift amount) which is an amount by which the blood vessel image 40 moves (shift amount) in order to make the position of the relative position coordinate Xn in the blood vessel image 40 coincide with the position of the relative position coordinate Xn in the fluoroscopic image 30. For example, in FIG. 9, a portion illustrated by a black circle is a portion in which the same relative position coordinate Xn is positioned. When two image are superimposed, positions of the black circles are shifted. The deviation at this time is the moving amount 13. Note that in FIG. 9, the blood vessel 11 is omitted. The moving amount 13 is obtained by being converted into the quantity of pixels based on the length of one side of one pixel. The control unit 3 is configured to perform control to acquire the length of one side of one pixel from the relative position relationship between the top board 1 and the imaging unit 2 and the irradiation angle of the X-ray source 21.

A threshold value of the moving amount 13 of the blood vessel image 40 is set in the X-ray imaging apparatus 100. The threshold value is set by, for example, a pixel quantity taking into account the effects of parallax. As shown in FIG. 8, the control unit 3 is configured to perform control, when the moving amount 13 of the acquired blood vessel image 40 is less than the threshold value, to move the blood vessel image 40 so as to be superimposed on the fluoroscopic image 30 and display the superimposed image 50 on the display unit 6. When the moving amount 13 of the acquired blood vessel image 40 is equal to or larger than the threshold value, the control unit 3 is configured not to perform control to move the blood vessel image 40, but to perform control to display only the fluoroscopic image 30 on the display unit 6. At this time, the control unit 3 may be configured to perform control to cause the display unit 6 to display a display warning that the blood vessel image 40 has not been moved and has not been superimposed on the fluoroscopic image 30.

The user 20 performs treatment while checking the superimposed image 50 displayed on the display unit 6, and selects a new blood vessel image 40 when changing the treatment position.

Referring to FIG. 1, FIG. 2, FIG. 6, FIG. 7, and FIG. 10, the setting in which the X-ray imaging apparatus 100 superimposes a peak hold image 42 and a fluoroscopic image 30 will be described.

In the case of the setting in which the X-ray imaging apparatus 100 superimposes a peak hold image 42 and a fluoroscopic image 30, unlike the setting of superimposing a blood vessel image 40 and a fluoroscopic image 30, the control unit 3 is configured to perform control to select a blood vessel image 40 having a lower pixel value for each relative position coordinate Xn from the storage unit 5. The control unit 3 is configured to perform control to acquire a moving amount 13 for each selected blood vessel image 40.

The control unit 3 is configured to perform control the image processing unit 4 to generate a peak hold image 42 from the selected plurality of blood vessel images 40.

As shown in FIG. 7, since the plurality of blood vessel images 40 is captured in accordance with the flow of the contrast agent, the position of the blood vessel 11 containing the contrast agent and the density of the contrast agent differ for each blood vessel image 40.

The image processing unit 4 performs processing of extracting each minimum pixel value of the relative position coordinates Xn of the plurality of blood vessel images 40 selected by the first selection. As shown in FIG. 7, portions where the plurality of blood vessel images 40 has a smaller pixel value (the portion with the thick line in FIG. 7) are different from each other. The image processing unit 4 is configured to connect the extracted portions of each of the plurality of blood vessel images 40 to generate a peak hold image 42 (see FIG. 10).

As shown in FIG. 10, after a peak hold image 42 is generated, the control unit 3 is configured to perform control to display a superimposed image 50 in which the peak hold image 42 and the fluoroscopic image 30 are superimposed on the display unit 6.

(Operation in Generating Blood Vessel Image)

Figure 11:
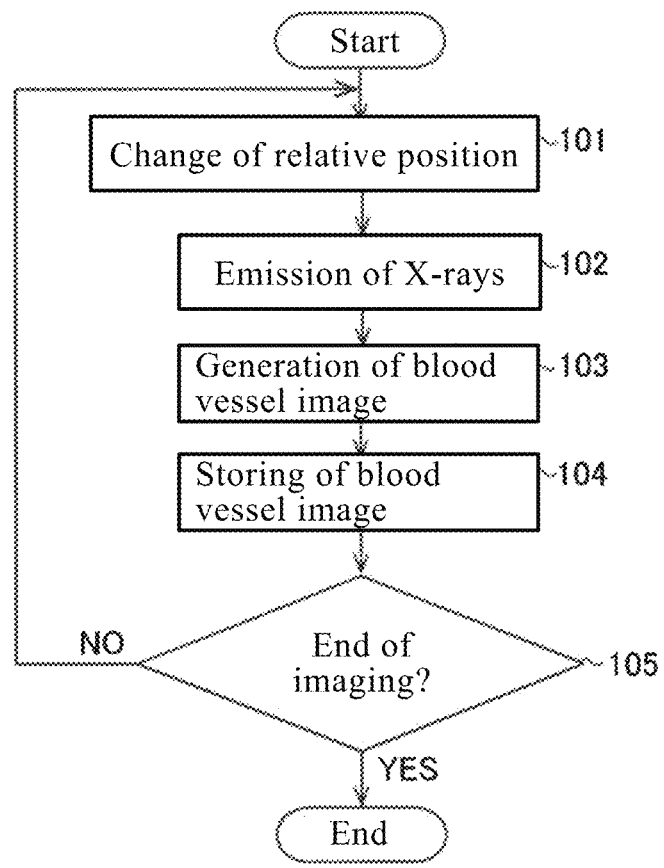
FIG. 11 is a flowchart showing the operation of the X-ray imaging apparatus when a blood vessel image is generated.

The operation of the X-ray imaging apparatus 100 in generating the blood vessel image 40 will be described with reference to FIG. 11.

In Step 101, the control unit 3 is configured to perform control to change the relative position between the top board 1 and the imaging unit 2 by moving the top board 1.

In Step 102, the control unit 3 is configured to perform control the X-ray source 21 to emit X-rays to the subject 10 to which a contrast agent has been administered.

In Step 103, the control unit 3 is configured to perform control the image processing unit 4 to generate a blood vessel image 40 based on a detection signal output from the detection unit 22.

In Step 104, the control unit 3 is configured to perform control to store the generated blood vessel image 40 in the storage unit 5.

In Step 105, when there is an input for ending imaging of the blood vessel image 40 from the user 20, the X-ray imaging apparatus 100 ends capturing of the blood vessel image 40. When there is no input from the user 20, the X-ray imaging apparatus 100 returns to Step 101 to continue capturing the blood vessel image 40.

(Operation in Displaying Superimposed Image)

Figure 12:
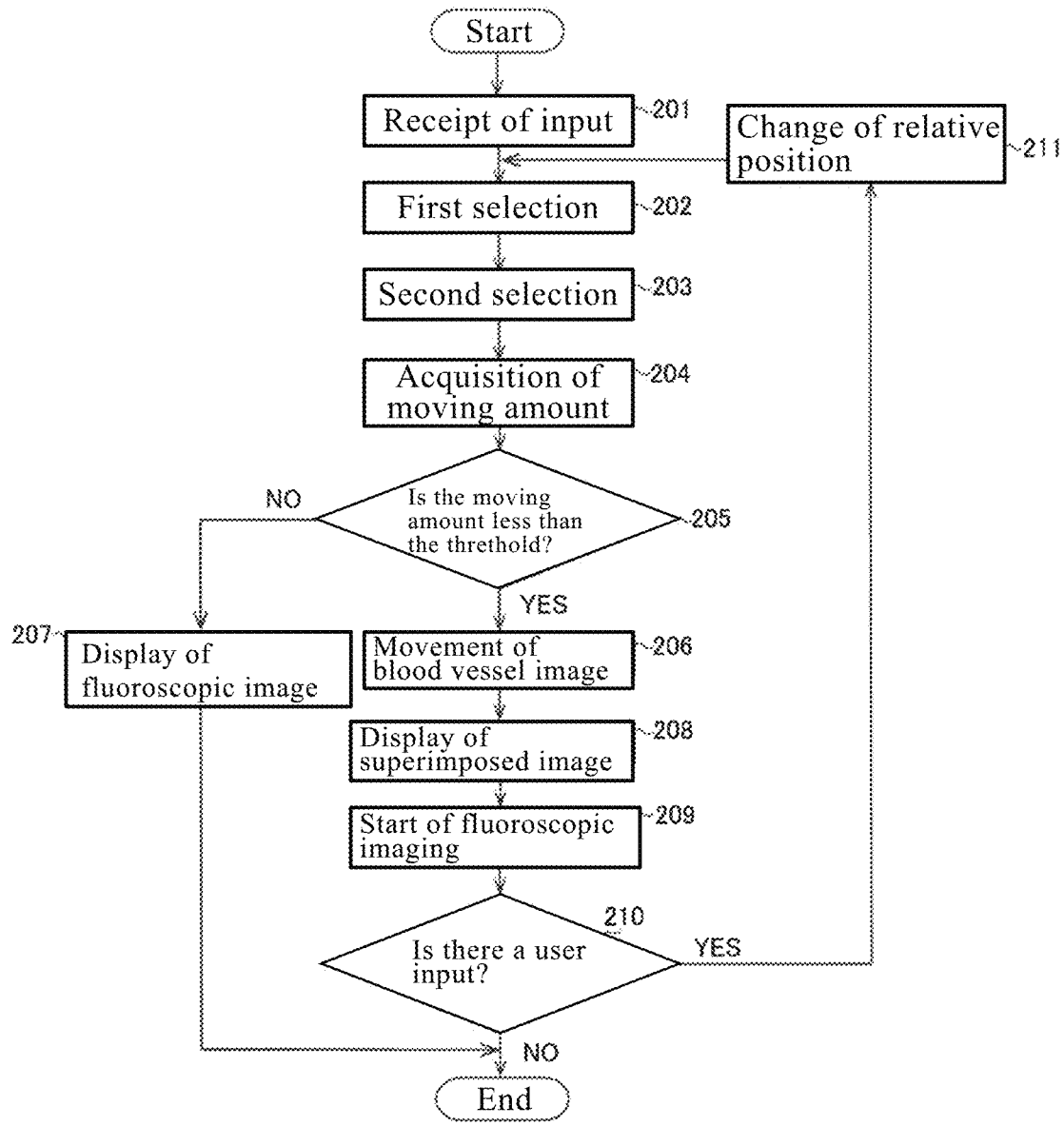
FIG. 12 is a flowchart showing the operation of the X-ray imaging apparatus when a superimposed image is displayed.

The operation of the X-ray imaging apparatus 100 in displaying the superimposed image 50 will be described with reference to FIG. 12 and FIG. 13. In FIG. 12, the X-ray imaging apparatus 100 is set so as to display not the peak hold image 42 but the superimposed image obtained by superimposing the blood vessel image 40 and the fluoroscopic image 30 on the display unit 6.

In Step 201, the X-ray imaging apparatus 100 accepts an input of initiation of fluoroscopic imaging of the user 20 at an imaging position where the fluoroscopic imaging is performed.

In Step 202, the control unit 3 is configured to perform control of a first selection to select a blood vessel image group 43 composed of a plurality of blood vessel images 40 including the same relative position coordinate Xn as the relative position coordinate Xn at the imaging position from the storage unit 5.

In Step 203, the control unit 3 is configured to perform control of a second selection to select a relative position coordinate Xn and one blood vessel image 40 in which the sum of pixel values at the relative position coordinate Xn and therearound is smallest from the blood vessel image group 43.

In Step 204, the control unit 3 is configured to perform control to acquire a moving amount 13 from the position of the relative position coordinate Xn of the selected blood vessel image 40 and the position of the relative position coordinate Xn of the fluoroscopic image 30.

In Step 205, the control unit 3 is configured to perform control differently depending on whether or not the acquired moving amount 13 is less than the threshold value.

In Step 206, the control unit 3 is configured to perform control to move the blood vessel image 40 when the acquired moving amount 13 is less than the threshold value.

In Step 207, the control unit 3 is configured to perform control to display the fluoroscopic image 30 on the display unit 6 without moving the blood vessel image 40 when the acquired moving amount 13 is equal to or larger than the threshold value. Then, the X-ray imaging apparatus 100 ends the operation of superimposing the fluoroscopic image 30 and the blood vessel image 40 and displaying the superimposed image.

In Step 208, the control unit 3 is configured to perform control to display a superimposed image 50 in which the selected blood vessel image 40 and the fluoroscopic image 30 are superimposed on the display unit 6.

In Step 209, the X-ray imaging apparatus 100 is configured to emit X-rays from the X-ray source 21 to initiate fluoroscopic imaging.

In Step 210, the operation of the control unit 3 differs depending on whether or not an input of the user 20 has been accepted. If the input of the user 20 has not been accepted, the fluoroscopic imaging ends.

When the input of the user 20 has been accepted, the process proceeds to Step 211, and the control unit 3 is configured to perform control to move the top board 1 to change the imaging position. After changing of the imaging position, the process returns to Step 202, and fluoroscopic imaging at the subsequent imaging position is performed.

Figure 13:
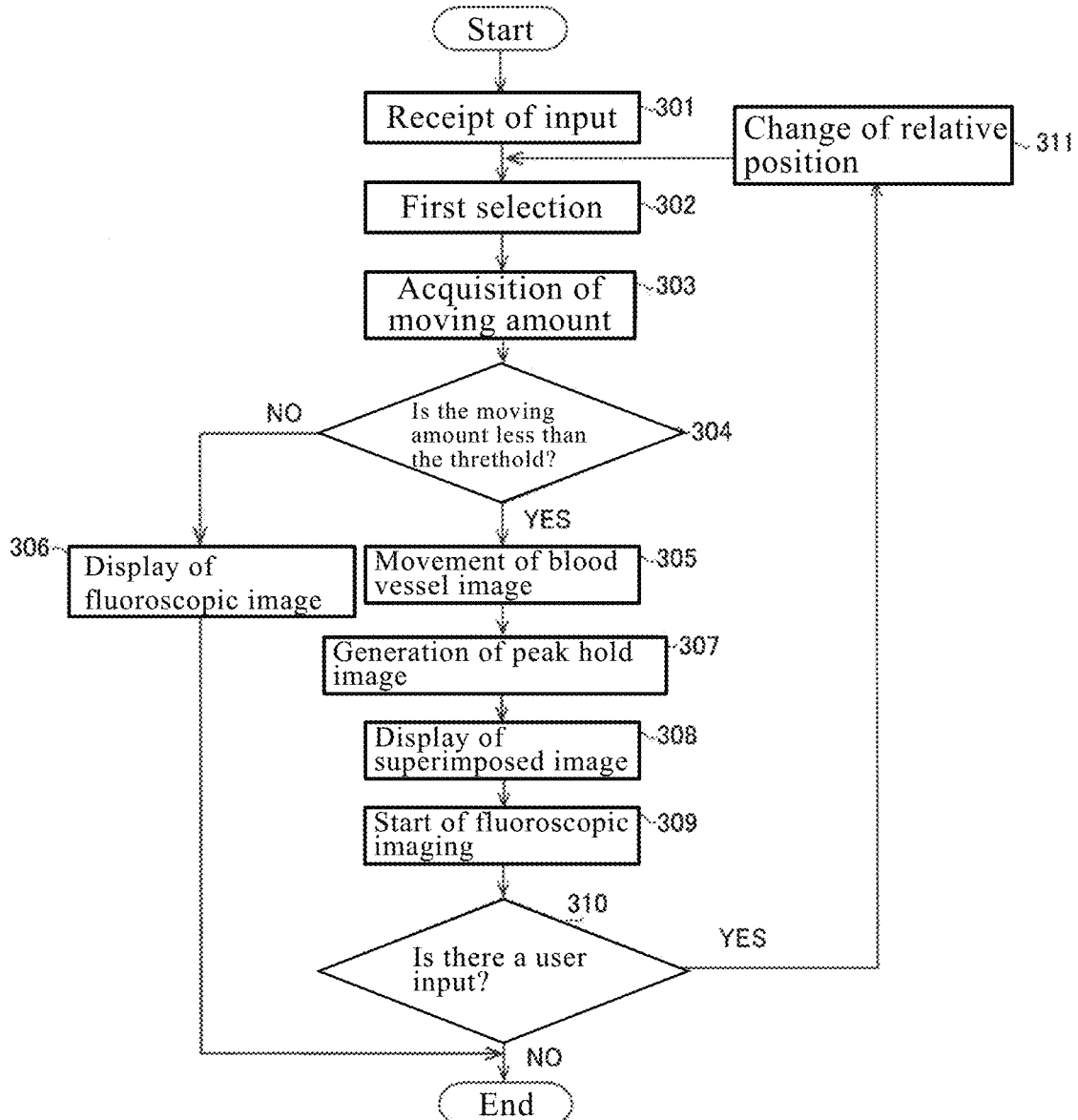
FIG. 13 is a flowchart showing another operation of the X-ray imaging apparatus when a superimposed image is displayed.

Referring to FIG. 13, the operation of the X-ray imaging apparatus 100 in displaying the superimposed image 50 will be described. In the figure, the X-ray imaging apparatus 100 is configured to set such that the peak hold image 42 and the fluoroscopic image 30 are superimposed and the superimposed image is displayed on the display unit 6.

In Step 301, the X-ray imaging apparatus 100 accepts an input of initiation of fluoroscopic imaging from the user 20 at the imaging position where fluoroscopic imaging is performed.

In Step 302, the control unit 3 is configured to perform control of the first selection to select from the storage unit 5 the blood vessel image group 43 composed of a plurality of blood vessel images 40 including the same relative position coordinate Xn as the relative position coordinate Xn at the imaging position.

In Step 303, the control unit 3 is configured to perform control to acquire the moving amount 13 from the position of the relative position coordinate Xn of the selected blood vessel image 40 and the position of the relative position coordinate of the fluoroscopic image 30.

In Step 304, the control unit 3 is configured to perform control differently depending on whether or not the acquired moving amount 13 is less than the threshold value.

In Step 305, the control unit 3 is configured to perform control to move the blood vessel image 40 when the acquired moving amount 13 is less than the threshold value.

In Step 306, the control unit 3 is configured to perform control to display the fluoroscopic image 30 on the display unit 6 without moving the blood vessel image 40 when the acquired moving amount 13 is equal to or larger than the threshold value. Then, the X-ray imaging apparatus 100 ends the operation of displaying the superimposed image 50 on the display unit 6.

In Step 307, the image processing unit 4 is configured to extract the lowest pixel value for each relative position coordinate Xn from the selected plurality of blood vessel images 40 and generate the peak hold image 42.

In Step 308, the control unit 3 is configured to perform control to display the superimposed image 50 in which the fluoroscopic image 30 and the peak hold image 42 are superimposed on the display unit 6.

In Step 309, the X-ray imaging apparatus 100 emits X-rays from the X-ray source 21 and starts fluoroscopic imaging.

In Step 310, the operation of the X-ray imaging apparatus 100 differs depending on whether or not the input from the user 20 has been accepted. When the input from the user 20 has not been accepted, the fluoroscopic imaging ends.

When the input from the user 20 has been accepted, the process proceeds to Step 311, and the control unit 3 is configured to perform control to move the top board 1 to change the imaging position. After the change of the imaging position, the process returns to Step 302, and fluoroscopic imaging at the subsequent imaging position is performed.

Effects of the Embodiment

In this embodiment, the following effects can be obtained.

In this embodiment, the X-ray imaging apparatus 100 is provided with a control unit 3 which performs at least one of control to select one blood vessel image 40 in which the blood vessel 11 is most clearly reflected from a plurality of blood vessel images 40 including the same relative position coordinate Xn as the imaging position of the fluoroscopic image 30 stored in the storage unit 5 and control to generate one blood vessel image 40 in which a blood vessel 11 is clearly reflected compared with each of a plurality of blood vessel images 40 including the same relative position coordinate Xn as the imaging position of the fluoroscopic image 30 stored in the storage unit 5, when capturing the fluoroscopic image 30 and performs control to display a superimposed image 50 in which one selected or generated blood vessel image 40 and a fluoroscopic image 30 are superimposed. With this, it is possible to select a blood vessel image 40 in which the same relative position coordinate Xn as the relative position coordinate Xn of the fluoroscopic image 30 is included and a blood vessel 11 is clear. As a result, a blood vessel image including the same relative position coordinate Xn as the fluoroscopic image 30 and clearly reflecting a blood vessel 11 can be easily selected from a plurality of blood vessel images 40. In addition, by generating one blood vessel image 40 in which a blood vessel 11 is clearly reflected compared with each of the plurality of blood vessel images 40 including the relative position coordinate Xn, it is possible to assuredly obtain an image in which a blood vessel 11 is clearly reflected.

In addition, in this embodiment, the control unit 3 is configured to perform, as control to select one blood vessel image 40 in which a blood vessel 11 is most clearly reflected out of a plurality of blood vessel images 40 including the same relative position coordinate Xn as the imaging position of the fluoroscopic image 30 stored in the storage unit 5, control of a first selection to select a blood vessel image group 43 composed of a plurality of blood vessel images 40 including the same relative position coordinate Xn as the imaging position of the fluoroscopic image 30 from the storage unit 5 and control of a second selection to select the blood vessel image 40 in which the blood vessel 11 is clearly reflected from a blood vessel image group 43 selected by the first selection. With this, since the blood vessel image group 43 including the relative position coordinate Xn of the fluoroscopic image 30 is selected by the control of the first selection, a blood vessel image 40 that can be superimposed on at least a part of the fluoroscopic image 30 is selected. In addition, since a blood vessel image 40 in which a blood vessel 11 is clearly reflected is selected from the blood vessel image group 43 selected by the control of the first selection by the control of the second selection, the blood vessel 11 can be clearly visually recognized in the superimposed image 50 in which the blood vessel image and the fluoroscopic image 30 are superimposed. Further, by separating the control of the first selection and the control of the second selection, compared with the case in which the control of the first selection and the control of the second selection are performed simultaneously, by performing the control of the first selection firstly, when the control of the second selection is performed, the number of blood vessel images 40 to be selected is reduced. Therefore, the control can be performed smoothly.

In addition, in this embodiment, the control unit 3 is configured to perform control to select the blood vessel image 40 in which the sum of pixel values at the relative position coordinate Xn and therearound is the smallest as a blood vessel image 40 in which a blood vessel 11 is clearly reflected in the second selection. Note that in a blood vessel 11 containing a contrast agent, X-rays are shielded by the contrast agent and therefore the pixel value becomes small, so that as a contrast agent is filled, the pixel value becomes smaller. So, in the blood vessel image 40 of the blood vessel 11 including a large amount of the contrast agent (filled with a contrast agent), the sum of the pixel values of the relative position coordinate Xn and therearound is small. Therefore, when the control unit 3 performs the control of selecting a blood vessel image 40 in which the sum of pixel values at the relative position coordinate Xn and therearound is the smallest as the control of the second selection, it is possible to select a blood vessel image 40 of a blood vessel 11 including a large amount of the contrast agent. Therefore, a blood vessel image 40 in which a blood vessel 11 is more clearly reflected can be selected.

Further, in this embodiment, the image processing unit 4 is configured to generate a long image 41 by connecting a plurality of blood vessel images 40 captured by administering a contrast agent, and the control unit 3 is configured to perform control to select a blood vessel image 40 in which a blood vessel 11 is clearly reflected from a plurality of blood vessel images 40 used for generating a long image 41. With this, since the blood vessel image 40 captured to generate a long image 41 is used, there is no need to capture a blood vessel image 40 to be superimposed on the fluoroscopic image 30. As a result, the X-ray exposure amount of the subject 10 can be reduced as compared with the case in which capturing of the blood vessel image 40 is performed because capturing of a blood vessel image 40 to be superimposed on the fluoroscopic image 30 is not performed.

In addition, in this embodiment, the control unit 3 is configured to accept one selection out of a plurality of blood vessel images 40 stored in the storage unit 5 and control the imaging unit 2 so as to perform fluoroscopic imaging at the relative position coordinate Xn of the selected blood vessel image 40. With this, since a fluoroscopic image 30 can be generated at the same imaging position as the selected blood vessel image 40, substantially the same image can be generated except for the difference in whether or not the blood vessel 11 is clear. As a result, since there is no positional shift between the blood vessel image 40 and the fluoroscopic image 30, it is possible to obtain a clear image of the superimposed image 50.

Further, in this embodiment, as described above, the control unit 3 is configured to perform control to move the blood vessel image 40 so that the relative position coordinate Xn in the selected blood vessel image 40 coincides with the relative position coordinate Xn in the fluoroscopic image 30. With this, even in cases where the imaging position of the blood vessel image 40 and the imaging position of the fluoroscopic image 30 are different, it is possible to use the blood vessel image 40 stored in the storage unit 5. As a result, it is not necessary to coincide the imaging position of the blood vessel image 40 with the imaging position of the fluoroscopic image 30, so that the user 20 can perform imaging at any imaging position. This makes it possible to increase the degree of freedom of imaging.

Further, in this embodiment, as described above, the control unit 3 is configured to perform the control to move the blood vessel image 40 when the moving amount 13 of the blood vessel image 40 is less than the threshold value and perform the control to not move the blood vessel image 40 and to not display the blood vessel image 40 when the moving amount 13 of the blood vessel image 40 is equal to or larger than the threshold value. With this, when the moving amount 13 is equal to or less than the threshold value, it is possible to generate an image in which the blood vessel image 40 and the fluoroscopic image 30 are superimposed. In addition, since the influence of parallax is caused by the position of the relative position coordinate Xn in the blood vessel image 40, it is possible to suppress the influence of parallax on the superimposed image 50 by not moving the moving amount 13 and not displaying the blood vessel image 40 when the moving amount 13 is equal to or larger than the threshold value.

In addition, in this embodiment, as the control to generate one blood vessel image 40 in which a blood vessel 11 is clearly reflected in comparison with each of the plurality of blood vessel images 40 including the same relative position coordinate Xn as the imaging position of the fluoroscopic image 30 stored in the storage unit 5, the control unit 3 is configured to perform control the image processing unit 4 so as to extract the minimum pixel value for each relative position coordinate Xn from the plurality of blood vessel images 40 and generate a peak hold image 42 and display the superimposed image 50 in which the generated peak hold image 42 and the fluoroscopic image 30 are superimposed on the display unit 6. As described above, in the blood vessel 11 in which a large amount of the contrast agent is contained, since the pixel value becomes small, it is possible to generate a blood vessel image 40 in which a large amount of the contrast agent is contained in the entire blood vessel by extracting the minimum pixel value for each relative position coordinate Xn from a plurality of blood vessel images 40. As a result, compared with the case in which the peak holding is not performed, the superimposed image 50 becomes an image in which the blood vessel 11 is entirely clear.

Further, in this embodiment, the image processing unit 4 is configured such that the image to be superimposed on the fluoroscopic image 30 can be switched between the blood vessel image 40 and the peak hold image 42 by setting. With this, the setting can be changed to the optimum setting in accordance with the imaging position, the imaging condition, and the like.

(Modifications)

It should be noted that the embodiment disclosed herein is to be considered in all respects as illustrative and not restrictive. The scope of the present invention is indicated by the appended claims rather than by the foregoing description of the embodiment, and the scope of the present invention includes all modifications (changes) within the meanings and ranges equivalent to the scope of the appended claims.

For example, in the above embodiment, an example is shown in which the X-ray imaging apparatus superimposes a blood vessel image used for generating a long image stored in a storage unit on a fluoroscopic image, but the present invention is not limited thereto. In the present invention, if a plurality of contrast agent images captured so as to include the same relative position coordinate is stored in a storage unit, a contrast agent image may not be used for generating a long image.

In the above embodiment, an example is shown in which the X-ray imaging apparatus changes the relative position between the imaging unit and the top board by moving the top board, but the present invention is not limited to this. In the present invention, the X-ray imaging apparatus may be configured to move the imaging unit to change the relative position between the imaging unit and the top board.

In the above embodiment, an example is shown in which the control unit is configured to move the blood vessel image so as to coincide the relative position coordinate in the selected blood vessel image with the relative position coordinate in the fluoroscopic image, but the present invention is not limited to this. In the present invention, the control unit may perform the control to display the superimposed image after selecting the blood vessel image without performing the control to move the blood vessel image.

In the above embodiment, an example is shown in which the control unit is configured to perform the control to move the top board so that the imaging position of the blood vessel image and the imaging position of the fluoroscopic image become the same based on the selection of the blood vessel image, but the present invention is not limited to this. In the present invention, fluoroscopic imaging may be performed by moving the top board by a user.

In the above embodiment, an example is shown in which the X-ray imaging apparatus is configured such that the image to be superimposed on the fluoroscopic image can be switched between a blood vessel image and a peak hold image by setting, but the present invention is not limited to this. According to the present inventio, the X-ray imaging apparatus may have only one of the setting of a blood vessel image and the setting of a peak hold image depending on the setting of an image to be superimposed on a fluoroscopic image.

(Mode)

It will be understood by those skilled in the art that the above described exemplary embodiments are concrete examples of the following aspects.

(Item 1)

An X-ray imaging apparatus, comprising:

a top board configured to place a subject thereon;

an imaging unit including an X-ray source configured to irradiate the subject placed on the top board with X-rays and a detection unit configured to detect X-rays transmitted through the subject and output a detection signal;

an image processing unit configured to generate a plurality of blood vessel images sequentially captured by administering a contrast agent to a blood vessel so that a plurality of images includes the same relative position coordinate while changing a relative position between the imaging unit and the top board and generate a fluoroscopic image captured at a timing different from timings of the plurality of blood vessel image images;

a storage unit configured to store the plurality of blood vessel images;

a display unit configured to display an image generated by the image processing unit; and a control unit configured to perform at least one of control to select one blood vessel image in which the blood vessel is most clearly reflected from the plurality of blood vessel images including the same relative position coordinate as an imaging position of the fluoroscopic image stored in the storage unit when the fluoroscopic image is captured and control to generate one blood vessel image in which the blood vessel is clearly reflected compared with each of the plurality of blood vessel images including the same relative position coordinate as the imaging position of the fluoroscopic image stored in the storage unit, and to perform control to display a superimposed image in which a selected or generated vessel image and the fluoroscopic image are superimposed on the display unit.

(Item 2)

The X-ray imaging apparatus as recited in the aforementioned Item 1, wherein the control unit is configured to perform, as control to select the one blood vessel image in which the blood vessel is most clearly reflected from the plurality of blood vessel images including the same relative position coordinate as the imaging position of the fluoroscopic image stored in the storage unit, control of a first selection to select a blood vessel image group composed of the plurality of fluoroscopic images including the same storage unit as the imaging position of the fluoroscopic image and control of a second selection to select the blood vessel image in which the blood vessel is clearly reflected from the blood vessel image group selected by the first selection.

(Item 3)

The X-ray imaging apparatus as recited in the aforementioned Item 2, wherein the control unit is configured to perform control to select the blood vessel image in which a sum of pixel values at the relative position coordinate and therearound is smallest as the blood vessel image in which the blood vessel is clearly reflected in the second selection.

(Item 4)

The X-ray imaging apparatus as recited in any one of the aforementioned Item 1 to 3, wherein the image processing unit is configured to connect the plurality of blood vessel images captured while administering the contrast agent to generate a long image, and wherein the control unit is configured to perform control to select the blood vessel image in which the blood vessel is clearly reflected from the plurality of blood vessel images used for generating the long image.

(Item 5)

The X-ray imaging apparatus as recited in any one of the aforementioned Items 1 to 4, wherein the control unit is configured to accept one selection of the plurality of blood vessel images stored in the storage unit and perform control of the imaging unit to perform fluoroscopic imaging at the relative position coordinate of the selected blood vessel image.

(Item 6)

The X-ray imaging apparatus as recited in any one of the aforementioned Items 1 to 5, wherein the control unit is configured to perform control to move the blood vessel image so as to coincide the relative position coordinate in the selected blood vessel image with the relative position coordinate in the fluoroscopic image.

(Item 7)

The X-ray imaging apparatus as recited in the aforementioned Item 6, wherein the control unit is configured to perform control to move the blood vessel image when a moving amount of the blood vessel image is less than a threshold value and control to not move the blood vessel image and not display a blood vessel image when the moving amount of the blood vessel image is equal to or greater than the threshold value.

(Item 8)

The X-ray imaging apparatus as recited in any one of the aforementioned Items 1 to 7, wherein the control unit is configured to control, as control to generate the one blood vessel image in which the blood vessel is clearly reflected compared with each of the plurality of blood vessel images including the same relative position coordinate as the imaging position of the fluoroscopic image stored in the storage unit, the image processing unit so as to generate a peak hold image composed by extracting a minimum pixel value each for the relative position coordinate from the plurality of blood vessel images and display a superimposed image in which the generated peak hold image and the fluoroscopic image are superimposed on the display unit.

(Item 9)

The X-ray imaging apparatus as recited in the aforementioned Item 8, wherein the image processing unit is configured such that an image to be superimposed on the fluoroscopic image is switched between the blood vessel image and the peak hold image by setting.

The invention claimed is:

1. An X-ray imaging apparatus, comprising:
a top board configured to place a subject thereon;
an imaging unit including an X-ray source configured to irradiate the subject placed on the top board with X-rays and a detection unit configured to detect X-rays transmitted through the subject and output a detection signal;
an image processing unit configured to generate a plurality of blood vessel images sequentially captured by administering a contrast agent to a blood vessel so that a plurality of images includes the same relative position coordinate while changing a relative position between the imaging unit and the top board and generate a fluoroscopic image captured at a timing different from timings of the plurality of blood vessel image images;
a storage unit configured to store the plurality of blood vessel images;
a display unit configured to display an image generated by the image processing unit; and
a control unit configured to perform at least one of control to select one blood vessel image in which the blood vessel is most clearly reflected from the plurality of blood vessel images including the same relative position coordinate as an imaging position of the fluoroscopic image stored in the storage unit when the fluoroscopic image is captured and control to generate one blood vessel image in which the blood vessel is clearly reflected compared with each of the plurality of blood vessel images including the same relative position coordinate as the imaging position of the fluoroscopic image stored in the storage unit, and to perform control to display a superimposed image in which a selected or generated vessel image and the fluoroscopic image are superimposed on the display unit.

2. The X-ray imaging apparatus as recited in claim 1, wherein the control unit is configured to perform, as control to select the one blood vessel image in which the blood vessel is most clearly reflected from the plurality of blood vessel images including the same relative position coordinate as the imaging position of the fluoroscopic image stored in the storage unit, control of a first selection to select a blood vessel image group composed of the plurality of fluoroscopic images including the same storage unit as the imaging position of the fluoroscopic image and control of a second selection to select the blood vessel image in which the blood vessel is clearly reflected from the blood vessel image group selected by the first selection.

3. The X-ray imaging apparatus as recited in claim 2, wherein the control unit is configured to perform control to select the blood vessel image in which a sum of pixel values at the relative position coordinate and therearound is smallest as the blood vessel image in which the blood vessel is clearly reflected in the second selection.

4. The X-ray imaging apparatus as recited in claim 1, wherein the image processing unit is configured to connect the plurality of blood vessel images captured while administering the contrast agent to generate a long image, and
wherein the control unit is configured to perform control to select the blood vessel image in which the blood vessel is clearly reflected from the plurality of blood vessel images used for generating the long image.

5. The X-ray imaging apparatus as recited in claim 1, wherein the control unit is configured to accept one selection of the plurality of blood vessel images stored in the storage unit and perform control of the imaging unit to perform fluoroscopic imaging at the relative position coordinate of the selected blood vessel image.

6. The X-ray imaging apparatus as recited in claim 1, wherein the control unit is configured to perform control to move the blood vessel image so as to coincide the relative position coordinate in the selected blood vessel image with the relative position coordinate in the fluoroscopic image.

7. The X-ray imaging apparatus as recited in claim 6, wherein the control unit is configured to perform control to move the blood vessel image when a moving amount of the blood vessel image is less than a threshold value and control to not move the blood vessel image and not display a blood vessel image when the moving amount of the blood vessel image is equal to or greater than the threshold value.

8. The X-ray imaging apparatus as recited in claim 1, wherein the control unit is configured to control, as control to generate the one blood vessel image in which the blood vessel is clearly reflected compared with each of the plurality of blood vessel images including the same relative position coordinate as the imaging position of the fluoroscopic image stored in the storage unit, the image processing unit so as to generate a peak hold image composed by extracting a minimum pixel value each for the relative position coordinate from the plurality of blood vessel images and display a superimposed image in which the generated peak hold image and the fluoroscopic image are superimposed on the display unit.

9. The X-ray imaging apparatus as recited in claim 8, wherein the image processing unit is configured such that an image to be superimposed on the fluoroscopic image is switched between the blood vessel image and the peak hold image by setting.

* * * * *